United States Patent
Gambardella et al.

(10) Patent No.: US 9,931,234 B2
(45) Date of Patent: Apr. 3, 2018

(54) PLANTAR FASCIITIS SLEEVE HAVING TARGETED COMPRESSION

(71) Applicant: Brownmed, Inc., Spirit Lake, IA (US)

(72) Inventors: Tamara Gambardella, Kansas City, MO (US); Brandon Rodriguez, Spirit Lake, IA (US); Matt Garver, Boston, MA (US)

(73) Assignee: Brownmed, Inc. (Delaware), Boston, MA (US)

( * ) Notice: Subject to any disclaimer, the term of this patent is extended or adjusted under 35 U.S.C. 154(b) by 288 days.

(21) Appl. No.: 14/628,856

(22) Filed: Feb. 23, 2015

(65) Prior Publication Data

US 2016/0242946 A1    Aug. 25, 2016

(51) Int. Cl.
    *A61F 13/00*      (2006.01)
    *A61F 5/01*      (2006.01)

(52) U.S. Cl.
    CPC ................... *A61F 5/0127* (2013.01)

(58) Field of Classification Search
    CPC ...................... A61F 5/0127; A61F 2013/00119
    USPC .......................................... 602/66, 75, 63, 28
    See application file for complete search history.

(56) References Cited

U.S. PATENT DOCUMENTS

| | | | |
|---|---|---|---|
| 2,589,241 A * | 3/1952 | Galhouse .................. | A61F 5/14 12/146 M |
| 3,050,053 A * | 8/1962 | Peckham ............ | A61F 5/05841 602/5 |
| 3,756,848 A | 9/1973 | Dahl | |
| 3,805,781 A * | 4/1974 | Hoey ..................... | A61F 13/066 602/65 |
| 3,934,583 A * | 1/1976 | Hollingshead ........ | A61F 5/0585 602/62 |
| 3,938,510 A * | 2/1976 | Gerber ................ | A61F 5/05875 602/22 |
| 5,645,525 A | 7/1997 | Krivosha | |
| 5,676,641 A * | 10/1997 | Arensdorf ............. | A61F 5/0111 602/27 |
| 5,938,631 A * | 8/1999 | Colman .................. | A61F 13/06 602/75 |
| 6,267,742 B1 | 7/2001 | Krivosha et al. | |
| 6,315,748 B1 * | 11/2001 | Morgan, Jr. .......... | A61F 13/104 128/878 |
| 6,641,550 B1 * | 11/2003 | Johnson ................ | A61F 5/0111 602/65 |
| 2003/0069530 A1 * | 4/2003 | Satou ................... | A61F 13/0273 602/75 |
| 2005/0015037 A1 * | 1/2005 | Oohira .................. | A61F 13/066 602/65 |
| 2011/0082403 A1 * | 4/2011 | Hill ....................... | A61F 5/0113 602/28 |

(Continued)

FOREIGN PATENT DOCUMENTS

JP      2001129015 A   *   5/2001
JP      2003268604 A   *   9/2003

*Primary Examiner* — Kim M Lewis
(74) *Attorney, Agent, or Firm* — McKee, Voorhees & Sease, PLC

(57) ABSTRACT

A foot sleeve is taught that has generalized sleeve compression from an elastic foot sleeve but also has targeted additional compression in the arch and above the heel across the Achilles tendon by a polymeric pressure sensitive adhesive tape applied as an X under the foot arch and in a preferred embodiment also across the Achilles tendon, just above the heel.

5 Claims, 3 Drawing Sheets

(56) References Cited

U.S. PATENT DOCUMENTS

| | | | |
|---|---|---|---|
| 2012/0136293 A1* | 5/2012 | Oosawa | A61F 5/0111 602/28 |
| 2014/0058311 A1* | 2/2014 | Higgins | A61F 13/08 602/63 |
| 2014/0276321 A1* | 9/2014 | Sellitto | A61F 5/0127 602/29 |
| 2015/0119781 A1* | 4/2015 | Ponce | A61F 5/0127 602/28 |
| 2016/0081836 A1* | 3/2016 | Sawle | A41B 11/007 602/28 |
| 2016/0100973 A1* | 4/2016 | Nelson | A61F 5/0127 602/23 |

* cited by examiner

PLANTAR FASCIITIS SLEEVE HAVING TARGETED COMPRESSION

FIELD OF THE INVENTION

The present invention relates to a foot sleeve having targeted compression for treatment of plantar fasciitis. It combines the advantages of taping with the convenience of a foot sleeve.

BACKGROUND OF THE INVENTION

Plantar fasciitis is one of the most common causes of heel pain, which accounts for approximately 15% of all foot-related complaints. This condition occurs in a wide variety of individuals. Commonly, age at onset is in the mid-40's, but plantar fasciitis can develop at any age, especially with athletes. Many studies have shown a female-male predominance of 3:1. 65% of patients exhibiting plantar fasciitis are overweight. Approximately 22% of all patients with plantar fasciitis have moderate pronation; about 15% have high-arched, ridge foot; and the remainder have an anatomically normal or non-affected foot. Only 45% of the patients who undergo radiography for suspected plantar fasciitis are found to have a subcalcaneal or "bone" spur.

Evidence of the need for affective therapy is apparent when it is considered that over 95% of all heel pain is diagnosed as plantar fasciitis. Plantar fasciitis is best described as an inflammation of the ligament that runs from the heel to the ball of the foot, which helps support the arch. Patients with plantar fasciitis will experience pain, upon standing, on the bottom or inside of their heel. Typically, the pain is worse in the morning when getting out of bed and after resting when standing up.

Typically the primary anatomic cause of plantar fasciitis is some degree of microtrauma and tearing at the site of the Plantar Fascia insertion. These abnormalities, which may also be present at the origin of the Plantar Fascia, result from repetitive trauma and collagen degeneration and angiofibroblastic hyperplasia. Upon physical examination the range of motion of the affected ankle is less than that of the contralateral ankle. By pressing the thumb against the middle of the affected heel, the physician can delineate the area of the Plantar Facial pain. Pressure similarly applied underneath the calcaneus reveals the area of subcalcaneal pain. The correlation between plantar fasciitis and subcalcaneal spurs is not significant, therefore radiographic findings are not specific. Conservative treatment, including night splints results in relief of plantar fasciitis in 85% of patients. In 15% of patients in whom this approach fails, surgery is indicated.

One medical method known in the art in reducing Plantar Fascial pain is to stretch the Plantar Fascia for a period of time. By keeping the Plantar Fascia on stretch, it is believed that an ultimate reduction of the internal tension of the Plantar Fascia can be achieved. Through this treatment, it is believed that the pain associated with this medical condition can be reduced, and possibly eliminated.

A typical treatment program for plantar fasciitis, depending on its severity includes taping, orthotic foot sleeves, even night splints for example of the type shown in U.S. Pat. No. 6,267,742 commonly and commonly assigned. All of the above have some advantages and some disadvantages.

It is no secret that perhaps one of the more effective treatments is taping but taping is of course inconvenient. First it must be renewed if not daily at least very frequently. Secondly it presents the extreme inconvenience to have to constantly tape and untape. Third, its effectiveness depends upon the skill level of the taping person.

Boots have the disadvantage of cumbersome and expense. Sleeves have a disadvantage of lack of targeted compression. As used herein "targeted compression" means compression at the specific points which would do the most good for plantar fasciitis, as opposed to overall general compression of the foot.

Accordingly it would be advantageous to provide the convenience of a sleeve with the advantages of targeted compression in the arch and heel area where compression treatment is most affective for plantar fasciitis.

This invention has as a primary objective to provide the convenience of a compression sleeve and the targeted effectiveness of enhancement of compression in the areas where it is most needed to affectively treat plantar fasciitis, namely in the arch and above the heel.

The method and manner of achieving this primary objective as well as other advantages of the invention is discussed hereinafter.

SUMMARY OF THE INVENTION

A foot sleeve is taught that has generalized sleeve compression from an elastic foot sleeve but also has targeted additional compression in the arch and above the heel across the Achilles tendon by a polymeric pressure sensitive adhesive tape applied as an X under the foot arch and in a preferred embodiment also across the Achilles tendon, just above the heel.

DETAILED DESCRIPTION OF THE PREFERRED EMBODIMENTS

Figure 1:
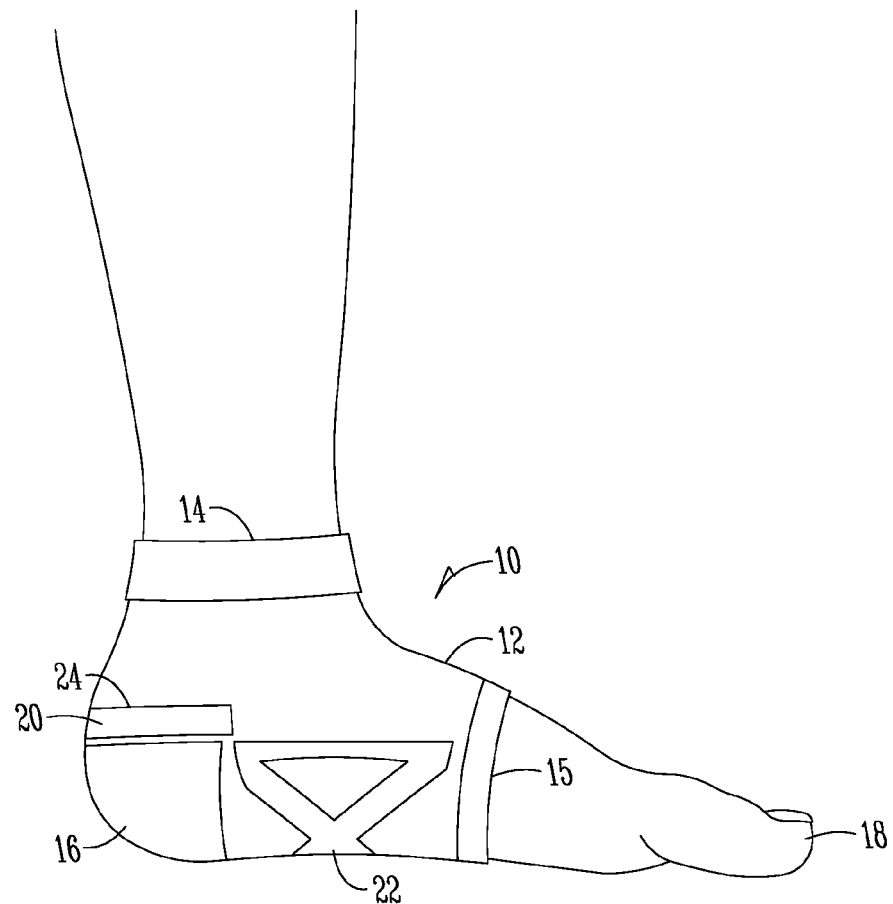
FIG. 1 is a view of a wearer's left foot showing the right side of the compression sock of the present invention.
Figure 2:
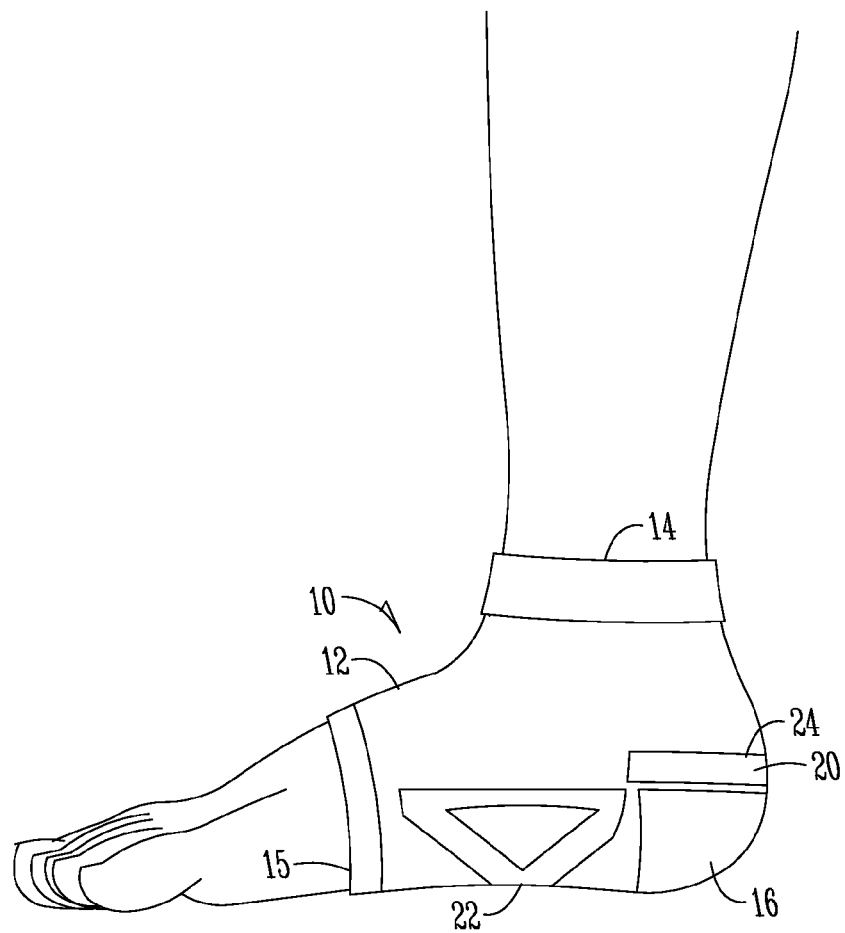
FIG. 2 is a left side view of the left foot showing the left side of the compression sock.
Figure 3:
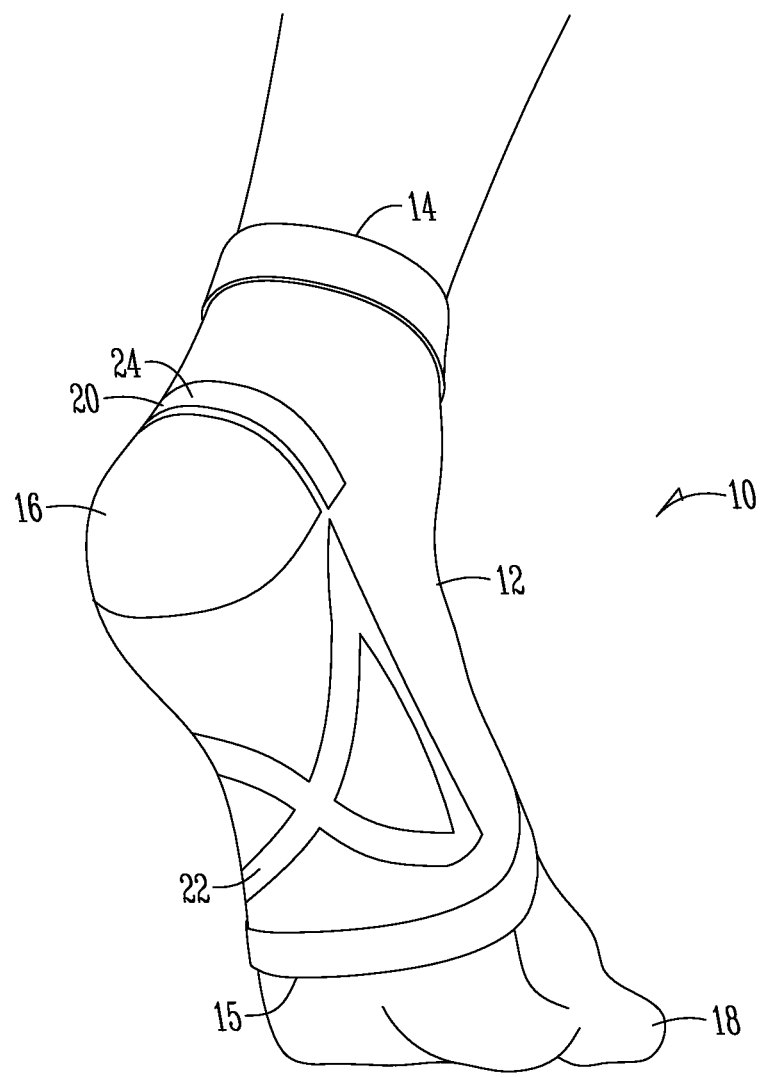
FIG. 3 is a perspective rear view showing the heel and bottom area of the sock.

FIGS. 1-3 show the preferred embodiment of the present invention. The foot sleeve 10 having targeted compression 10 is comprised of a half stocking 12 having an open top 14 and an open forward end 15. The sleeve 10 is made of a stretchable material so as to fit snuggly around the posterior, lateral, medial and plantar aspects of the heel 16 of the foot 18. The foot sleeve 10 of targeted compression is made of any one of many stretchable elastic compression materials well known and available in the art. When worn the foot sleeve 10 applies a general overall uniform pressure to the entire foot it surrounds. As earlier explained such sleeves as just described are well known and have been routinely available for long periods of time. What is missing from such sleeves is the concept of targeted compression, that is targeting their compressive affect not to the entire foot area but in a different manner to the area where treatment is most needed for plantar fasciitis, i.e., in the arch of the foot and above the heel.

The targeted compression of the present invention is accomplished by applying a polymeric pressure sensitive adhesive tape 20 as an X 22 under the foot arch and also as a band above the Achilles heels 24.

High temperature polyurethane pressure sensitive adhesive tapes are known, see for example U.S. Pat. No. 3,756, 848, patented Sep. 4, 1973, which is incorporated herein by reference. The polyurethane pressure sensitive adhesive tape applied as an X under the arch and as a band at the top of the heel disrupts the natural stretch of the elastic sleeve and promotes greater pull and compression in the targeted compression regions. Ultimately the X lifts the arch and distributes the pressure evenly across the foot. The X 22 stretch design mimics taping methods typically recommended by professionals and the band 24 of like tape across the heel disrupts the heel pain that typically accompanies plantar fasciitis and Achilles tendonitis.

As earlier expressed the tape may be that available through a variety of commercial sources. However the critical thing is that the tape must have greater compressive force than the material from which the foot sleeve is made. For example one suitable foot sleeve material is lycra and the tape in that instance must have a greater compressive force, i.e., strength of stretchability than the foot sleeve itself. The tape can be transparent and/or colored polyurethane tapes with or without the support of polyamide and can come in a variety of colors to match or contrast with the sleeve. Suitable tapes can be those sold under the trademark Oeko-tex by Framis, spa. Tape when applied with heated pressure sticks to the sleeve and attaches to it, lasting as long as the sleeve itself. Moreover it is washable without damage to the tape or its adhesive properties.

Certain constructional features are worthy of mention. The X configuration with the sides of the X connected as depicted in FIG. 3 provides for further compressive affect to duplicate the affect of taping. Specifically the X stretch with the X opposing sides filled in i.e., and the Achilles tendon band of the same tape material distribute greater pressure in the areas of the foot specifically needed to treat plantar fasciitis. The preferred material for the sock itself is material that is 58% nylon, 26% bamboo charcoal polyester, and 16% lycra. Bamboo charcoal polyester is a natural plant fiber and has benefits of antibacterial, deodorizing, and quick to dry. In addition different tapes of different compressive forces may be used to selectively treat mild, moderate, or severe cases of plantar fasciitis, in other words strength of the compressiveness can be matched to the severity of the case.

It can be seen that the invention accomplishes at least all of its stated objectives.

What is claimed is:

1. A foot sleeve for a person having a foot arch and heel, said sleeve having targeted compression, comprising:
    an elastic compression sleeve adapted to fit around the foot arch and heel of a person, having a front toe opening and a top ankle opening, and a foot arch area; and
    a polymeric pressure sensitive adhesive tape, applied to the foot sleeve under the foot arch area of the foot sleeve in an X-shape and to the foot sleeve as a band above the Achilles heel, to provide targeted additional compression, said polymeric pressure sensitive adhesive tape having greater compressive properties than said sleeve.

2. The foot sleeve of claim 1 wherein the polymeric pressure sensitive tape is polyurethane tape.

3. The foot sleeve of claim 2 wherein the polymeric pressure sensitive adhesive tape is heat and pressure sensitive tape.

4. The foot sleeve of claim 1 wherein the X-shape is adapted to be applied under the foot arch and has a top, bottom and opposing sides with each of the opposing sides having a connecting polymeric strip of tape extending from the top to the bottom, for even further targeted compression.

5. The foot sleeve of claim 1 wherein the foot sleeve and polymeric pressure sensitive adhesive tape are washable without damage to the polymeric pressure sensitive adhesive tape or its adhesive properties.

* * * * *